US011468977B2

(12) United States Patent
Roy et al.

(10) Patent No.: US 11,468,977 B2
(45) Date of Patent: Oct. 11, 2022

(54) METHOD AND SYSTEM FOR INTERPRETING NEURAL INTERPLAY INVOLVING PROPRIOCEPTIVE ADAPTATION DURING A DUAL TASK PARADIGM

(71) Applicant: Tata Consultancy Services Limited, Mumbai (IN)

(72) Inventors: Sangheeta Roy, Kolkata (IN); Oishee Mazumder, Kolkata (IN); Kingshuk Chakravarty, Kolkata (IN); Debatri Chatterjee, Kolkata (IN); Aniruddha Sinha, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 554 days.

(21) Appl. No.: 16/587,309

(22) Filed: Sep. 30, 2019

(65) Prior Publication Data
US 2020/0135324 A1  Apr. 30, 2020

(30) Foreign Application Priority Data
Oct. 25, 2018 (IN) .............................. 201821040329

(51) Int. Cl.
*G16H 20/30* (2018.01)
*G06F 30/20* (2020.01)
(Continued)

(52) U.S. Cl.
CPC ............ *G16H 20/30* (2018.01); *A61B 5/1114* (2013.01); *A61B 5/1116* (2013.01); *A61B 5/389* (2021.01);
(Continued)

(58) Field of Classification Search
CPC ......... G16H 20/30; G06F 30/20; G06F 3/015; A61B 5/389; A61B 5/1114; A61B 5/1116;
(Continued)

(56) References Cited

U.S. PATENT DOCUMENTS

| 2013/0035613 A1* | 2/2013 | Curtiss | ................. A61B 5/4023 600/595 |
|---|---|---|---|
| 2013/0123665 A1* | 5/2013 | Mariani | ............... A61B 5/6807 600/592 |

(Continued)

FOREIGN PATENT DOCUMENTS

| EP | 3298955 | 3/2018 |
| WO | WO-2017/158569 | 9/2017 |

OTHER PUBLICATIONS

Ghai, S. et al. (2017). "Effects of dual tasks and dual-task training on postural stability: a systematic review and meta-analysis," *Clinical Interventions in Aging*, vol. 12; pp. 557-577.

*Primary Examiner* — Jay Trent Liddle
*Assistant Examiner* — Alyssa N Brandley
(74) *Attorney, Agent, or Firm* — Finnegan, Henderson, Farabow, Garrett & Dunner LLP (57) ABSTRACT

Collision avoidance and postural stability adjustment may provide an effective dual task paradigm to interpret the effect of proprioceptive adaptation on balance control. However, conventionally tasks are physical tasks performed under supervision in specific set up environments. Implementations of the present disclosure provide methods and systems for interpreting neural interplay involving proprioceptive adaptation in a lower limb during a dual task paradigm. The disclosed method provides a better interpreting of the neuronal mechanisms underlying adaptation and learning of skilled motor movement and to determine the relationship of lower limb proprioceptive sense and postural stability by simulating integration of a Single Limb Stance (SLS) func-
(Continued)

tionality test for postural stability and a single limb collision avoidance task, in an adaptive Virtual Reality (VR) environment provided to a subject.

9 Claims, 5 Drawing Sheets

(51) Int. Cl.
  *A61B 5/11* (2006.01)
  *A61B 5/00* (2006.01)
  *A63B 24/00* (2006.01)
  *G06F 3/01* (2006.01)
  *A61B 5/389* (2021.01)
(52) U.S. Cl.
  CPC .......... *A61B 5/744* (2013.01); *A63B 24/0062* (2013.01); *G06F 3/015* (2013.01); *G06F 30/20* (2020.01); *A61B 2505/09* (2013.01); *A63B 2024/0096* (2013.01)
(58) Field of Classification Search
  CPC . A61B 5/744; A61B 2505/09; A63B 24/0062; A63B 2024/0096
  See application file for complete search history.

(56) References Cited

U.S. PATENT DOCUMENTS

| | | | |
|---|---|---|---|
| 2017/0231532 A1* | 8/2017 | Chakravarty | A61B 5/6897 600/595 |
| 2017/0270818 A1* | 9/2017 | French | G09B 5/02 |
| 2018/0121728 A1* | 5/2018 | Wells | G02B 27/0176 |

* cited by examiner

METHOD AND SYSTEM FOR INTERPRETING NEURAL INTERPLAY INVOLVING PROPRIOCEPTIVE ADAPTATION DURING A DUAL TASK PARADIGM

PRIORITY CLAIM

The present application claims priority from Indian provisional patent application no. 201821040329, filed on Oct. 25, 2018. The entire contents of the aforementioned application are incorporated herein by reference.

TECHNICAL FIELD

The disclosure herein generally relates to field of functionality tests for proprioceptive adaptation, and, more particularly, to a method and system understanding neural interplay involving proprioceptive adaptation in lower limb during a dual task paradigm.

BACKGROUND

Postural stability is an integral component of the motor control and coordination process, carried out by interaction within proprioceptive afferents and complex sensory motor actions. Postural instability is one of the prominent symptom associated with geriatric population and is a major precursor for fall. Use of a dual-task training paradigm to enhance postural stability in subjects, typically patients, with balance impairments is an emerging area of interest. Research has been carried out in dual task paradigm to have a better understanding on task prioritization and neural interplay. Thus, to be more precise and accurate in understanding on task prioritization and neural interplay associated with a body part of the subject, defining or designing appropriate dual task paradigm in accordance with the body part to be analyzed is critical. More accurate the understanding of the neural interplay for the tasks to being performed enables providing right guidance and training to the subject, for example during rehabilitation.

Dual task paradigm has been studied by researchers to find the effects of distribution of attention or other cognitive resources in order to perform both tasks efficiently. Typically, dual task involving lower limbs can be either motor dual task, which requires simultaneous activity of a balance task and any motor task; or cognition dual task, which integrates postural control with cognitive loading. Both types of dual task are noted as ways of training patients with neurological damage to recover their motor control ability. As research mentions, a complex dual task, exhibiting coordination between stability and motor action can be represented by the 'stepping over an obstacle task'. Precise control of foot trajectory over an obstacle is a skilled motor task, which requires effective sensory motor integration of visual and proprioceptive input along with information about motor commands. It has been known that adaptation to a new locomotor skill occurs during repetitive stepping over an obstacle, mostly due to proprioception. Proprioception also plays an important role in motor skill acquisition.

There has been substantial research on understanding effect of proprioceptive adaptation typically focused on only upper limb control, effect of postural control during cognitive loading, and collision avoiding strategies involving visual information storage. Further, the existing research on dual task paradigm often limits to the patient being subjected to actually performing the dual task under supervision such as in physiotherapy clinics. The requirement of physical performance such as walking on treadmill while performing second task is not helpful and may be risky with patient already having the disability to perform. Possibility of hurting the patient or the subject remain high and may not be most appropriate way to monitor and train a patient.

SUMMARY

Embodiments of the present disclosure present technological improvements as solutions to one or more of the above-mentioned technical problems recognized by the inventors in conventional systems. For example, in one aspect, there is provided a processor implemented method for understanding neural interplay involving proprioceptive adaptation during a dual task paradigm, the method comprising: monitoring, by one or more hardware processors, a subject performing the dual task paradigm, wherein the dual task paradigm is performed by the subject with a lower limb, from both limbs of the subject, at predefined intervals for a predefined time period for understanding the neural interplay involving proprioceptive adaptation in the lower limb of the subject while performing the dual task paradigm. The dual task paradigm comprises simulating integration of a Single Limb Stance (SLS) functionality test for postural stability and a single limb collision avoidance task, in an adaptive Virtual Reality (VR) environment provided to the subject, wherein the subject is positioned on an object in the VR environment equipped with one of a VR head set for immersive environment and a display screen for non-immersive environment, Electromyography (EMG) sensors placed on muscles associated with ankle joints of both limbs of the subject, and wherein motion of the subject while performing the dual task paradigm is sensed using a set of motion sensors placed at a predefined distance from the object. Further, the method comprises receiving, by the one or more hardware processors, data associated with the subject performing the dual task paradigm, wherein the data comprises metadata of an avatar of the subject from the VR head set, data from the EMG sensors and data from the set of motion sensors, to estimate a plurality of model parameters for the subject, wherein the plurality of model parameters comprise a Centre of Mass (CoM) sway, a collision rate, a trajectory smoothness variation and a muscle co-activation of the subject for the dual task paradigm. Furthermore, the method comprises analyzing, by the by one or more hardware processors, variation in the CoM sway, the collision rate, the trajectory smoothness variation and the muscle co-activation estimated for the subject in accordance with the dual task paradigm performed by the subject at the predefined intervals for the predefined time period to understand the neural interplay involving proprioceptive adaptation in the lower limb during the dual task paradigm, wherein analysis provides a task that subject prioritizes among postural stability and collision avoidance in the dual task paradigm.

In another aspect, there is provided a system for understanding neural interplay involving proprioceptive adaptation during a dual task paradigm. The system comprises a memory storing instructions; one or more Input/Output (I/O) interfaces; and one or more hardware processors coupled to the memory via the one or more communication interfaces, wherein the one or more hardware processors are configured by the instructions to monitor a subject performing the dual task paradigm, wherein the dual task paradigm is performed by the subject with a lower limb, from both limbs of the subject, at predefined intervals for a predefined time period for understanding the neural interplay involving proprioceptive adaptation in the lower limb of the subject while performing the dual task paradigm. The dual task paradigm comprises: simulating integration of a Single Limb Stance (SLS) functionality test for postural stability and a single limb collision avoidance task, in an adaptive Virtual Reality (VR) environment provided to the subject, wherein the subject is positioned on an object in the VR environment equipped with one of a VR head set for immersive environment and a display screen for non-immersive environment, Electromyography (EMG) sensors placed on muscles associated with ankle joints of both limbs of the subject, and wherein motion of the subject while performing the dual task paradigm is sensed using a set of motion sensors placed at a predefined distance from the object. Furthermore, the one or more hardware processors are configured to receive data associated with the subject performing the dual task paradigm, wherein the data comprises metadata of an avatar of the subject from the VR head set, data from the EMG sensors and data from the set of motion sensors, to estimate a plurality of model parameters for the subject, wherein the plurality of model parameters comprise a Centre of Mass (CoM) sway, a collision rate, a trajectory smoothness variation and a muscle co-activation of the subject for the dual task paradigm (204). Furthermore, analyze variation in the CoM sway, the collision rate, the trajectory smoothness variation and the muscle co-activation estimated for the subject in accordance with the dual task paradigm performed by the subject at the predefined intervals for the predefined time period to understand the neural interplay involving proprioceptive adaptation in the lower limb during the dual task paradigm, wherein analysis provides a task that subject prioritizes among postural stability and collision avoidance in the dual task paradigm.

In yet another aspect, there are provided one or more non-transitory machine readable information storage media comprising one or more instructions which when executed by one or more hardware processors causes a method for monitoring a subject performing the dual task paradigm, wherein the dual task paradigm is performed by the subject with a lower limb, from both limbs of the subject, at predefined intervals for a predefined time period for understanding the neural interplay involving proprioceptive adaptation in the lower limb of the subject while performing the dual task paradigm. The dual task paradigm comprises simulating integration of a Single Limb Stance (SLS) functionality test for postural stability and a single limb collision avoidance task, in an adaptive Virtual Reality (VR) environment provided to the subject, wherein the subject is positioned on an object in the VR environment equipped with one of a VR head set for immersive environment and a display screen for non-immersive environment, Electromyography (EMG) sensors are placed on muscles associated with ankle joints of both limbs of the subject, and wherein motion of the subject while performing the dual task paradigm is sensed using a set of motion sensors placed at a predefined distance from the object. Further, the method comprises receiving data associated with the subject performing the dual task paradigm, wherein the data comprises metadata of an avatar of the subject from the VR head set, data from the EMG sensors and data from the set of motion sensors, to estimate a plurality of model parameters for the subject, wherein the plurality of model parameters comprise a Centre of Mass (CoM) sway, a collision rate, a trajectory smoothness variation and a muscle co-activation of the subject for the dual task paradigm. Furthermore, the method comprises analyzing variation in the CoM sway, the collision rate, the trajectory smoothness variation and the muscle co-activation estimated for the subject in accordance with the dual task paradigm performed by the subject at the predefined intervals for the predefined time period to understand the neural interplay involving proprioceptive adaptation in the lower limb during the dual task paradigm, wherein analysis provides a task that subject prioritizes among postural stability and collision avoidance in the dual task paradigm.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

A dual task paradigm which can simulate the effect of collision avoidance as well as maintaining postural stability, is not a strong focusses area of research. Given the prominent role of proprioceptive feedback in motor control, it may be expected that the acquisition of skilled motor performance, like collision avoidance could be related to lower limb proprioceptive sense. Collision avoidance and postural stability adjustment may provide an effective dual task paradigm to understand the effect of proprioceptive adaptation on balance control.

Embodiments of the present disclosure provide methods and systems for understanding neural interplay involving proprioceptive adaptation in a lower limb during a dual task paradigm. The disclosed method provides a better understanding of the neuronal mechanisms underlying adaptation and learning of skilled motor movement and to determine the relationship of lower limb proprioceptive sense and postural stability by simulating integration of a Single Limb Stance (SLS) functionality test for postural stability and a single limb collision avoidance task, in an adaptive Virtual Reality (VR) environment provided to a subject. The subject performing the task at predefined intervals for a predefined time period is monitored. A plurality of model parameters comprising a Centre of Mass (CoM) sway, a collision rate, a trajectory smoothness variation, a muscle co-activation and the like are estimated for the subject in accordance with the dual task paradigm performed by the subject at the predefined intervals for the predefined time period. Analysis of variation in the model parameters over the predefined time period is performed, which enables understanding the neural interplay involving proprioceptive adaptation in the lower limb. The analysis enables to identify a task that subject prioritizes among postural stability and collision avoidance in the dual task paradigm. Thus, to understand the neural interplay between maintaining postural stability and acquiring a skilled motor task in terms of collision avoidance, the method discloses a VR game, designed as the dual task paradigm. The game is played using a set of motion sensors such as Microsoft Kinect™ and the VR environment such as provided by a Google VR™ box. In an embodiment, the game may be played without a VR head set with game being displayed on a large screen in front of the subject.

Referring now to the drawings, and more particularly to FIGS. 1 through 5, where similar reference characters denote corresponding features consistently throughout the figures, there are shown preferred embodiments and these embodiments are described in the context of the following exemplary system and/or method.

Figure 1:
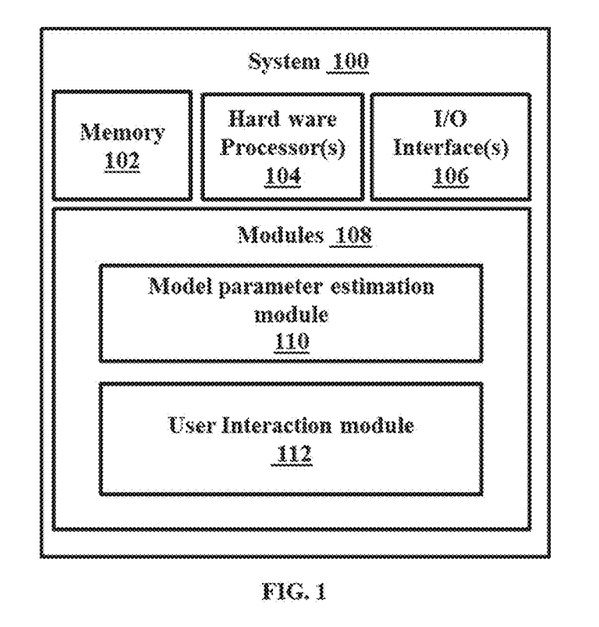
FIG. 1 illustrates an exemplary block diagram of a system for understanding neural interplay involving proprioceptive adaptation in a lower limb during a dual task paradigm, in accordance with an embodiment of the present disclosure.

FIG. 1 illustrates an exemplary block diagram of a system 100 for understanding the neural interplay involving proprioceptive adaptation in the lower limb during the dual task paradigm, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 may be one or more software processing modules (not shown) and/or one or more hardware processors as shown in FIG. 1. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the hardware processor(s) 104 is configured to fetch and execute computer-readable instructions stored in the memory 102. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices such as to a VR for immersive environment and a display screen for non-immersive environment, Electromyography (EMG) sensors, a set of motion sensors and the like. The I/O interfaces 106 also enables communication of the system 100 with a server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, a plurality of modules 108 can be stored in the memory 102, wherein the modules 108 may comprise a model parameter estimation module 110 and a user interaction module 112. The model parameter estimation module 110, when executed by the one or more processors (one or more hardware processors) 104, can be configured to perform estimation and analysis of the plurality of model parameters for the understanding neural interplay involving proprioceptive adaptation in the lower limb of the subject during the dual task paradigm. The user interaction module 112, when executed by the one or more processors (one or more hardware processors) 104, can be configured to instruct and guide the subject with steps for performing the dual task paradigm and provide instant feedback based on current performance of the subject. The functions of the model parameter estimation module 110 and the user interaction module 112 are explained in conjunction with FIG. 2, FIG. 3 and FIG. 4. The memory 102 may further comprise information pertaining to input(s)/output(s) of each step performed by model parameter estimation module 110 and the user interaction module 112 and other modules (not shown) of the system 100 and methods of the present disclosure. For example, the memory may store the estimated values of the plurality of model parameters comprising the CoM sway, the collision rate, the trajectory smoothness variation, the muscle co-activation and the like, and also the analysis performed based on the variation observed in the model parameters. The system 100, through the I/O interface 106 may be coupled to external data sources.

Figure 2:
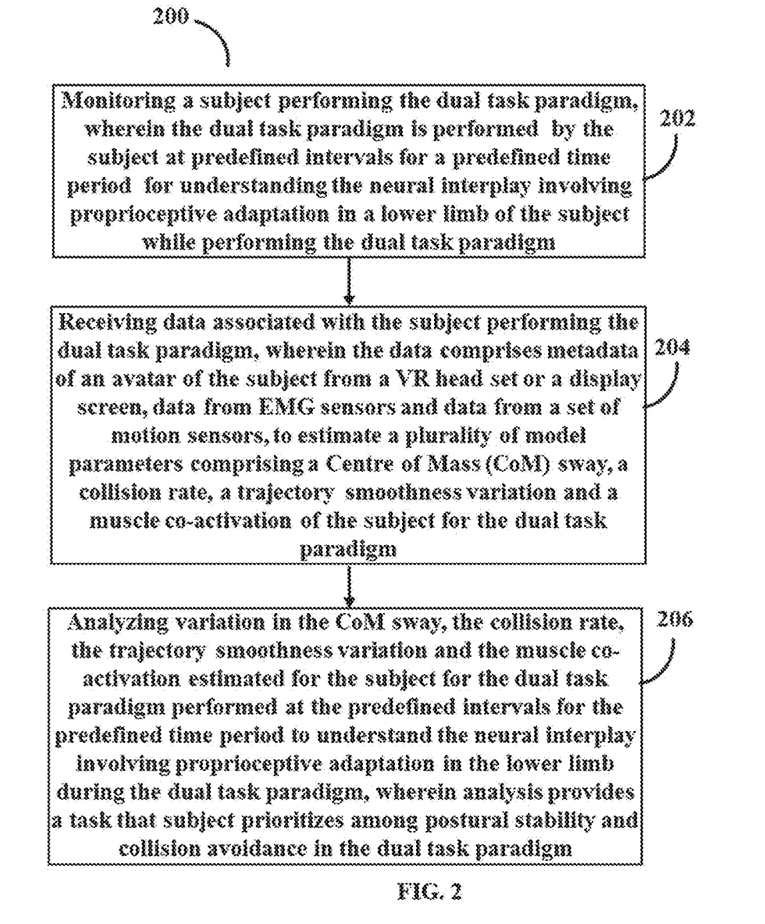
FIG. 2 illustrates an exemplary flow diagram of a method, implemented by the system of FIG. 1, for understanding the neural interplay involving proprioceptive adaptation in the lower limb during the dual task paradigm, in accordance with an embodiment of the present disclosure.

FIG. 2 illustrates an exemplary flow diagram of a method 200, implemented by the system of FIG. 1, for understanding the neural interplay involving proprioceptive adaptation in the lower limb during the dual task paradigm, in accordance with an embodiment of the present disclosure. In an embodiment, the system(s) 100 comprises one or more data storage devices or the memory 102 operatively coupled to the one or more hardware processors 104 and is configured to store instructions for execution of steps of the method 200 by the one or more processors 104 in conjunction with various modules such as the model parameter estimation module 110 and the user interaction module 112 of the modules 108. The steps of the method 200 of the present disclosure will now be explained with reference to the components of the system 100 as depicted in FIG. 1, and the steps of flow diagram as depicted in FIG. 2. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Figure 3:
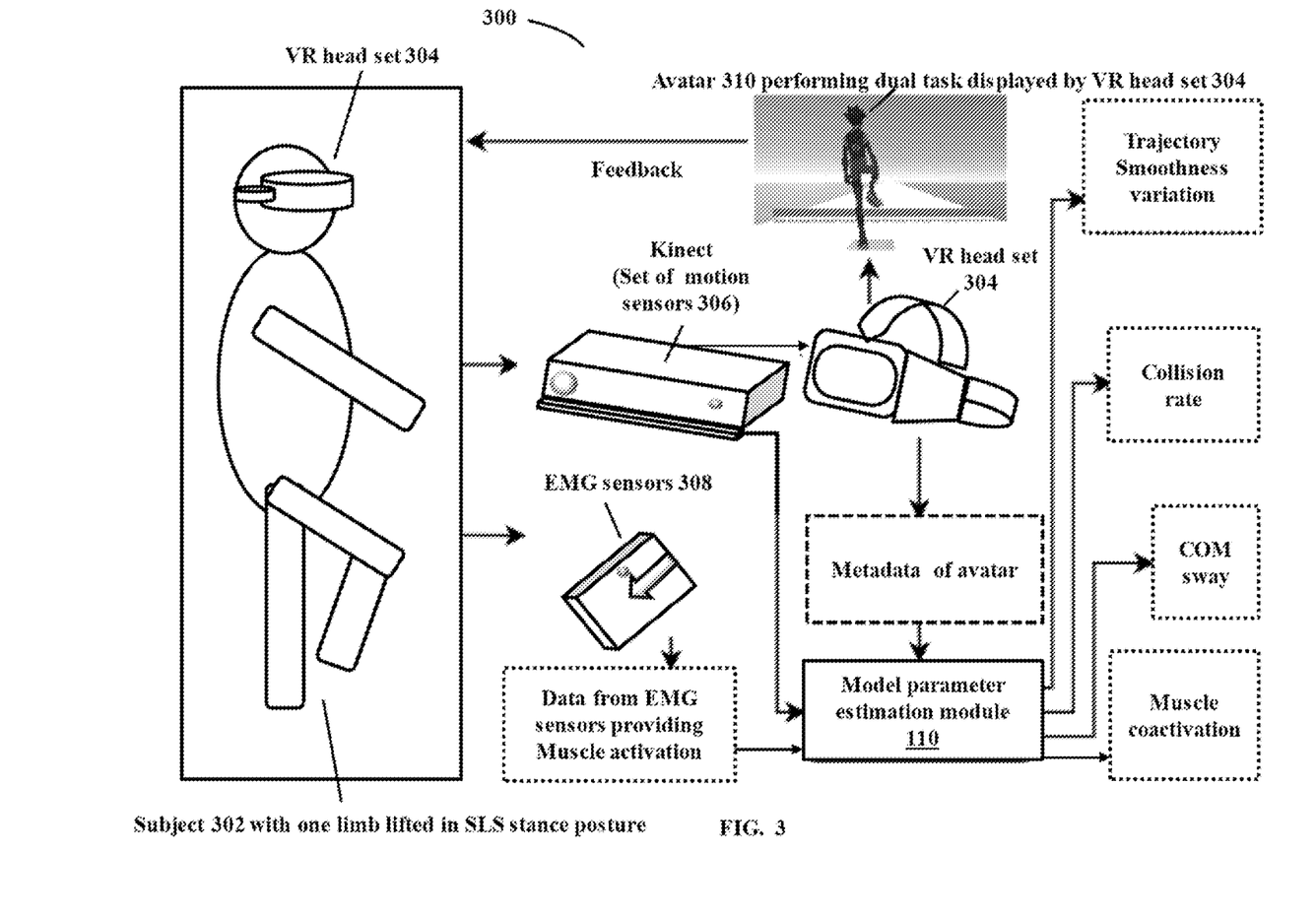
FIG. 3 illustrates an example Virtual Reality (VR) environment of system of FIG. 1 for understanding the neural interplay involving proprioceptive adaptation in the lower limb during the dual task paradigm, in accordance with an embodiment of the present disclosure.
Figure 4A:
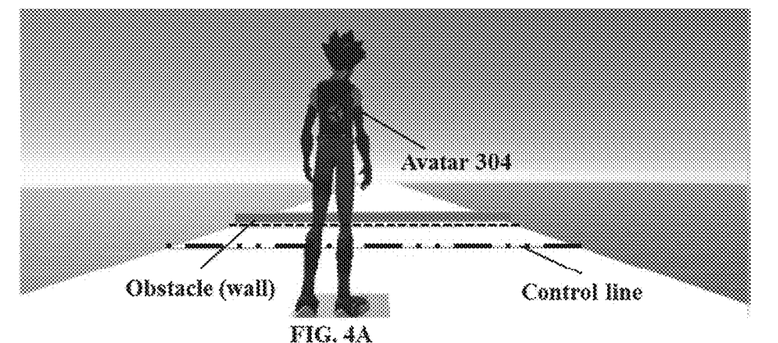
FIG. 4A, FIG. 4B and FIG. 4C illustrate sequence of action of an avatar of a subject performing the dual task paradigm, in accordance with an embodiment of the present disclosure.
Figure 4B:
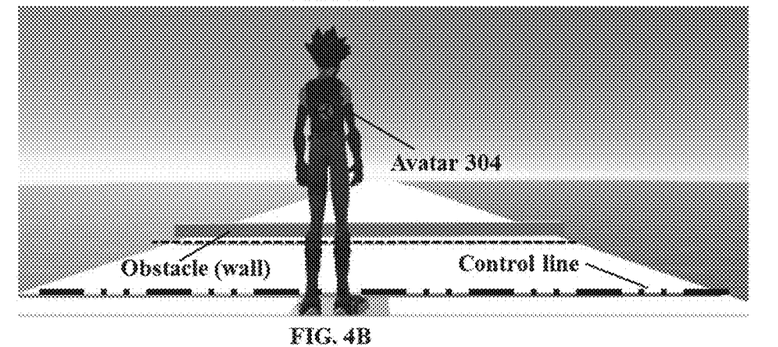
Figure 4C:
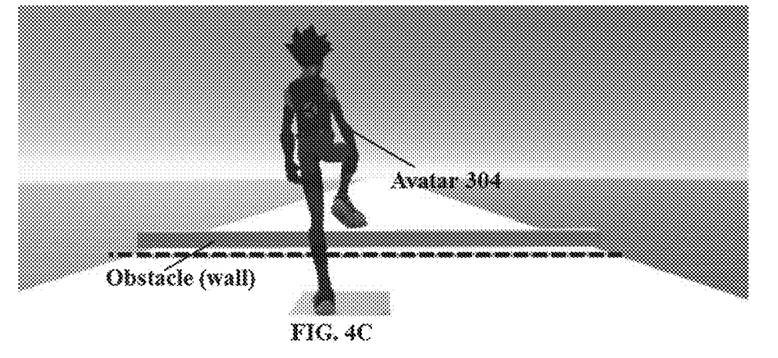

In an embodiment, prior to estimation and analysis for the plurality of model parameters, a subject 302 is instructed to understand the dual paradigm task (game) to be performed in the VR environment 300 as depicted in FIG. 3. The user interaction module 112 is configured to instruct the subject to be monitored while performing the dual task paradigm. The subject 302 is instructed to stand on an object with both limbs (alternatively referred as both lower limbs) of the subject resting on the object. The subjects rest position is as depicted in FIG. 4A with an avatar of the subject 302 displayed on the VR headset or the display screen. Further, the user interaction module 112 is configured to display a trail of control lines and obstacles of a predefined height approaching the avatar in the VR environment 300 the subject 302, wearing a VR head set 304 (for example, Google VR™ box), as depicted in FIG. 4B. In an embodiment, when opted for non-immersive environment by the subject 302, the user interaction module is configured to display the trail of control lines and the obstacles on the display screen such as a large TV screen (not shown). Further, the subject is instructed to lift the lower limb for a SLS posture when both limbs of the avatar touch a control line in the approaching trail. The subject 302 is instructed to hold the SLS posture till an obstacle in the trail is crossed over by the avatar, as depicted in FIG. 4C. Further, the subject 302 is instructed to perform the task for a predefined time interval (for example say 15 minutes every day) and asked to repeat the dual task paradigm for a predefined period (for example, 5 days). During the dual task paradigm, the user interaction module 112 is configured to notify the subject 302 of success or failure in maintaining the SLS posture and crossing of the obstacle. The subject 302 is also provided with a feedback for corrective action improve the collision avoidance in the SLS posture in real time. For example, if the subject's limb (leg) touches the virtual object or obstacle (herein "wall"), the obstacles visual appearance as seen by the subject changes, for example, the obstacle color changes can from green to red. Thus, a change in visual appearance, for example herein a change in color, is a feedback indication of subject's own action. This indicates the subject to correct his action, from next step onward, such as further lifting the leg a bit more to avoid the obstacle.

Thus, the subject 302 acts as an avatar in the VR game and performs a single leg collision avoidance task while maintaining stability in the SLS posture. During this event, model parameters like the trajectory of the limb used to avoid obstacle, body sway (CoM sway), number of collision, and muscle activity of two specific muscles, naming Tibialis Anterior (TA) and Lateral Gastrocnemius (LG) are acquired and processed to extract information related to postural stability, proprioceptive action and rate of learning and adaptation.

FIG. 4A through FIG. 4C illustrate sequence of action of the avatar of the subject 302 performing the dual task paradigm. For example, an adaptive VR based training task is developed using cross platform game engine Unity 5.5.1f1. The environment depicts SLS functional task to highlight the postural stability variation. The SLS functional task, interchangeably referred as SLS test, provides a quick, reliable and easy method to assess static stability, fall risk and functional evaluation of geriatric population. The Google VR™ and headphones are used to produce the visceral feeling of actually being in the simulated world by placing the subject 302 in a 3D environment. The immersive environment is created by surrounding the subject of the VR system with the avatar, a 3D space containing various components which work as visual cues to users to perform the task, and sound that provide an absorbing environment.

For example, a game, simulating the designed dual task paradigm, integrates the collision avoidance task while maintaining balance in SLS posture. In the VR environment 300, subject 302 stands in front of a large display floor on an object (for example, an instructed mat or simply referred as mat). A 'control line' (dotted and dashed line in FIG. 4A and FIG. 4B) and obstacle (in shape of say 'wall' with 'X color') at a height of 35 cm, appear moving towards the subject 302. The control line generates sound when it touches feet (limbs) of the subject's 302, instructing the subject 302 to uplift say right leg according to SLS posture. Subject 302, needs to perceive the wall (obstacle) height and hold his/her position until the wall crosses the avatar. The uplifted leg (limb in SLS posture) is tracked whether it hits the 'wall' or not. In case of a correct avoidance of obstacle, the wall color remains 'X color', indicating one successful run. If collision occurs, color of the wall changes to 'Y color', guiding the subject about the result and helping to form a neural inference in terms of motor learning to modify its action in subsequent trials.

Advantage of the disclosed dual task paradigm designed to be performed in the VR environment is that there is no hard and fast requirement of an expert to be around as the dual paradigm task is a game to be played in VR environment, wherein the subject is monitored by estimating the plurality of model parameters, which are also recorded for any future analysis by the expert. The improvement in subject's performance can be analyzed from the estimated plurality of model parameters. Further, post analysis from an expert the difficulty level of the dual paradigm task (game) can be increased to further train the subject. For example, the difficulty level can be increase by randomizing the occurrence and height of the obstacle.

Monitoring the subject, and estimation of model parameters can be performed in real time for instantaneous report provided to an expert. For understanding the neural interplay involving proprioceptive adaptation in the lower limb of the subject while performing the dual task paradigm, in an embodiment, at step 202 of the method 200, the parameter estimation module 110 is configured to monitor the subject 302 performing the dual task paradigm. The dual task paradigm is performed by the subject at the predefined intervals for the predefined time period. The dual task paradigm comprises simulating integration of the SLS functionality test for postural stability and a single limb collision avoidance task, in an adaptive Virtual Reality (VR) environment 300 provided to the subject 302. The subject 302 is positioned on the object in the VR environment wearing the VR head set 304, Electromyography (EMG) sensors 308 placed on muscles associated with ankle joints of both limbs of the subject 302. Further, data associated with motion of the subject while performing the dual task paradigm is sensed using a set of motion sensors 306 (for example, Microsoft Kinect™) placed at a predefined distance from the mat. For each predefined time interval, at step 204 of the method 200, the model parameter estimation module 110 is configured to receive data associated with the subject 302 performing the dual task paradigm. In example herein, when using the Kinect™ sensors, the predefined distance is about 182.88 centimeters. The data comprises metadata of the avatar of the subject 302 from the VR head set 304, data from the EMG sensors 308 and data from the set of motion sensors 306, used to estimate the plurality of model parameters for the subject 302.

Estimation of the plurality of model parameters comprising the CoM sway, the collision rate, the trajectory smoothness variation and the muscle co-activation of the subject 302 for the dual task paradigm is described below.

1) Sway analysis: Postural stability and sway are highly correlated parameters. Numerous experimental studies suggest that subjects who exhibit larger sway during quiet standing have poorer postural stability. The set of motion sensors 306 (for example, Kinect™ V2) records 3D spatio-temporal information of twenty-five joints of the subject 302 during the dual task paradigm. The acquired joint information is filtered using Multivariate de-noising, which implements a procedure combining wavelet transform and Principal component analysis (PCA). The CoM sway is calculated using statistically equivalent serial chain (SESC) model. Shoulder center and hip center of a Kinect™ skeleton is considered as the start and end point of the serial chain. Midpoint of this chain is estimated to be the body CoM. Projection of the estimated CoM is equivalent to body sway. Sway area is calculated using convex hull algorithm on the estimated CoM variations during SLS.

Figure 5:
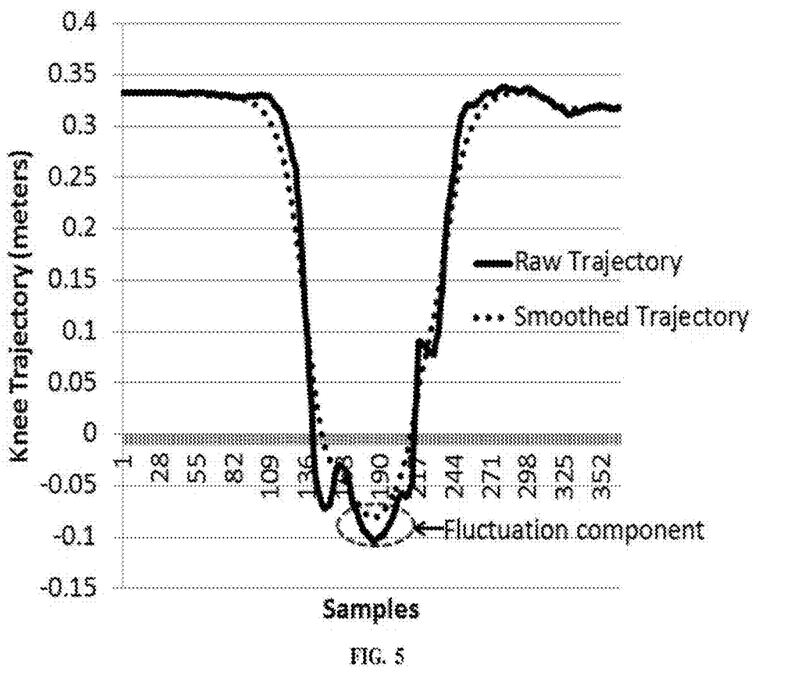
FIG. 5 is a graph illustrating analysis of a smoothness function on trajectory response during the dual task paradigm performed by the subject, in accordance with an embodiment of the present disclosure.

2) Trajectory smoothness variation: It has been hypothesized that the trajectory of the limb, which is performing the collision avoidance task, and SLS improves due to the proprioceptive adaptation over trials. The slow and fast varying components of spatio-temporal trajectory of 3D knee coordinates contain information associated with visually guided proprioceptive learning of neural states. The disclosed method 200 determines slow and fast varying fluctuation components in a knee trajectory as depicted in the graph of FIG. 5 and tracks them over trials, which provides information about the degree of discomfort and learning time. Spatio-temporal variation in knee coordinates (forming the trajectory) with respect to Hip center coordinates is analyzed. In order to find the fast varying components, the data $y_i(t)$ representing the difference between knee Y coordinates (in Y direction) with respect to Hip-center's Y coordinates at time t (where $t \in [0, T]$ and T=one trial interval for trial i(≤N) are converted into functional form, which generates a functional series $\{t_i, y_i(t)\}, \forall i=1 \ldots N$ where $$y_i(t) = f_i(t) + \sigma_i(t)\varepsilon_{t,i} \quad (1)$$

Where $\varepsilon_{t,i}$ independent and identically distributed standard normal random variable and $\sigma_i(t)$ allows for the amount of noise to vary with t. In equation 2 below, f(t) is approximated as linear combination of a set of K basis functions $\phi_k$ and is expressed as:

$$f(t) = \Sigma_{k=1}^{K} a_k \phi_k \quad (2)$$

The coefficients $a_k$ is determined by minimizing the objective function shown in (3) using iterative optimization:

$$J = \Sigma_{t=1}^{T} [y_i(t) - f_i(t)]^2 + \lambda * PEN(f) \quad (3)$$

where, PEN(f) is a measure of roughness and is defined as $$\int \frac{d^4}{dt^4} - f(t)^2,$$

λ is the smoothing parameter to balance the fitting. Since in this case, observed data sequence (raw signal) for any trial is aperiodic in nature, the signal is converted into functional form using a set of 300 B-spline basis functions of order 5.

Order has been selected heuristically. High frequency fluctuation in the data is obtained by setting $\lambda=10^2$. Change in trajectory variation over trial time thus can be assumed as the measure of neural intervention and adaptation due to the designed proprioception. The graph on the FIG. 5 shows the smoothed trajectory response during the dual task.

3) Muscle co-activation or EMG co-activation is the simultaneous activation of agonist and antagonist muscle groups around a joint. Muscle co-activation modulates the impedance of a joint, mainly stabilizing the joint. Co-activation of antagonist muscles is observed in motor learning. Previous researches have shown that co-activation of muscles declines as learning progresses, both when subjects learn stable as well as unstable dynamical tasks. The muscle co-activation around the ankle joint of both the limbs are acquired using the EMG sensors 308, for example Delsys™ EMG sensors, placed over A and LG muscle. Raw EMG signals are acquired at 1000 Khz frequency. Moving window RMS (Root Mean Square) technique as in equation 4 below is applied to compute RMS for each successive incoming EMG data sample with 200 millisecond (ms) overlapping window after bias correction.

$$x_{RMS} = \sqrt{\frac{1}{N} \sum_{i=1}^{N} x_i^2} \quad (4)$$

where, N specifies the window length and $x_i$ is the instantaneous, amplitude of raw EMG value at the $i^{th}$ sample. Ratio between EMG RMS acquired from TA and LG muscle over the trial periods generate the co-activation function.

At step 206 of the method 200, the model parameter estimation module 110 is configured to analyze variation in the CoM sway, the collision rate, the trajectory smoothness variation and the muscle co-activation estimated for the subject in accordance with the dual task paradigm performed by the subject at the predefined intervals for the predefined time period to understand the neural interplay involving proprioceptive adaptation in the lower limb during the dual task paradigm. The analysis to identify variation can be performed automatically wherein a submodule in the model parameter estimation module follows instructions that interpret the variations as defined by an expert. For example, based on record of subject's previous performance on the similar task, the improvement in term of model parameters can be identified automatically. The automated analysis may be further confirmed with the expert prior to further usage. The analysis enables interpreting of the task that subject prioritizes among postural stability and collision avoidance in the dual task paradigm. Further the analyzed variation in the CoM sway, the collision rate, the trajectory smoothness variation and the muscle co-activation providing interpreting of the neural interplay involving proprioceptive adaptation in the lower limb of the subject is used to design personalized rehabilitation therapy for the subject.

Results and Discussions

The CoM Sway, the collision rate, the trajectory smoothness variation and the muscle co-activation of five subjects under study are analyzed for change in these parameters over trial as well as role of retention and habituation of the proprioceptive effect over a span of four days.

TABLE 1

| Subject | Smoothness variation | | | Sway (MM) | | | Collision | | | EMG (SLS) | | | EMG (non-SLS) | | |
|---|---|---|---|---|---|---|---|---|---|---|---|---|---|---|---|
| (Yrs) | I | II | III | I | II | III | I | II | III | I | II | III | I | II | III |
| S1-38M | 29 | 23 | 21 | 22.49 | 18.32 | 16.74 | 6 | 5 | 1 | 0.4 | 0.28 | 0.27 | 0.83 | 0.83 | 0.87 |
| S2-30F | 19 | 16 | 16 | 36.95 | 39.37 | 49.09 | 7 | 1 | 1 | 0.53 | 0.41 | 0.41 | 0.73 | 0.78 | 0.78 |
| S3-29M | 21 | 20 | 20 | 23.78 | 31.29 | 17.54 | 8 | 3 | 1 | 0.48 | 0.31 | 0.32 | 0.81 | 0.81 | 0.82 |
| S4-36M | 26 | 21 | 18 | 16.34 | 17.89 | 18.24 | 22 | 16 | 6 | 0.61 | 0.42 | 0.42 | 0.76 | 0.76 | 0.75 |
| S5-33M | 28 | 25 | 20 | 29.36 | 37.97 | 53.16 | 7 | 8 | 4 | 0.68 | 0.53 | 0.51 | 0.88 | 0.87 | 0.87 |

Table 1 shows the variation of learning or adaptation parameters and body sway over the trial period. 60 cycle trial period has been divided in to three groups, named I, II and III of 20 trials each to understand the effect of proprioception, as number of trials increase and the subject becomes more habituated with the dual task paradigm. As hypothesized, variation in trajectory decreases over trial period in all subjects, indicating the effect of learning and adaptation to suit the purpose of the skilled motor activity. Number of collision also decreases over the trial period, the most number of collision occurring during the initial trials and progressively decrease as number of trials increases. EMG co-activation of the associated ankle muscle of the limb undergoing SLS and collision avoidance shows a progressive decrease in their value, indicating the effect of learning and ankle adaptation. The adaptation is evident after 15 to 20 trial cycles and remain fixed thereafter. Co-activation of the other limb however shows no evident change in muscle activity as there is no learning or adaptation strategy to be followed. This limb supports the body mass when the other limb is adapting to the changes, hence the activation may increase as trial increases. The sway parameter on the other hand do not follow any predictable trend during the course of trial. Sway indicates the postural stability adjustment that the subject makes during the course of experiment to maintain their balance. In the dual task of maintaining stability and avoiding collision, neural control prioritizes balance over occurrence of collision in virtual environment.

trajectory smoothness is not directly correlated. Collision avoidance is less prioritized if postural instability creeps in. So, even if the trajectory response is optimized to avoid collision, if the body sway increase, chance of collision will also increase.

The method thus provides the dual task paradigm designed in the VR environment, which has least risk of any damage to the subject during the test as he/she does not have physically walk on a treadmill, or in case he/she loses the balance in the SLS posture or while crossing the obstacle hurt does not in reality fall over the obstacle, but on the object where he/she performs the task. Further, unlike conventional methods where such tasks require supervision, and need to be often performed at specific clinics, the method and system disclosed does not necessarily require assistance to perform the dual task paradigm and receives feedback to improve the task performed. The designed dual task paradigm simulated in the VR environment is typically important when subject being monitored is already disabled or aged. Thus, the designed game for the dual task paradigm provides a more comfortable test platform. The dual task paradigm in VR incorporates the dynamicity of real time. Here, the subject needs to step over by avoiding obstacle (without touching the wall in VR game) while he is in single limb stance (SLS) and in motion virtually. In this design, the difficulty of adaptation can be increased by increasing the height, speed of the obstacle and speed of virtual path (where subject stands). So, parameters of obstacle (speed,

TABLE 2

| Subject (Yrs) | Smoothness variation | | | | Sway (mm) | | | | Collision | | | |
|---|---|---|---|---|---|---|---|---|---|---|---|---|
| | D1 | D2 | D3 | D4 | D1 | D2 | D3 | D4 | D1 | D2 | D3 | D4 |
| S1-38M | 43 | 36 | 22 | 20 | 19.5 | 20.93 | 36.36 | 30.34 | 12 | 9 | 9 | 11 |
| S2-30F | 28 | 23 | 20 | 16 | 32.91 | 33.22 | 35.16 | 43.10 | 11 | 8 | 9 | 9 |
| S3-29M | 38 | 31 | 24 | 17 | 20.44 | 17.73 | 19.23 | 18.41 | 14 | 6 | 6 | 2 |
| S4-36M | 43 | 31 | 33 | 21 | 14.58 | 18.63 | 17.49 | 19.46 | 32 | 28 | 14 | 12 |
| S5-33M | 28 | 24 | 24 | 23 | 25.45 | 29.59 | 39.74 | 27.31 | 19 | 17 | 7 | 4 |

Table 2 shows the effect of retention of proprioceptive adaptation over a span of four days. Smoothness variation, sway and number of collisions have been analyzed for all five subjects for four days of trial period (D1, D2, D3, and D4). There is an evident change in trajectory smoothness parameter, variation of which decreases as the subject becomes more habituated with the experiment on a daily basis. This indicates that information about the trajectory response is retained with the help of proprioception. Sway area shows no evident pattern, again indicating that neural control re-invests separately for maintaining postural control and its priority is higher in dual task paradigm. Number of collisions also decreases as the subject becomes more adapted over the durations. However, rate of collision and height) and duration of SLS can be varied according to patient requirement. Therefore, the subject with postural instability, can be monitored thoroughly at home rather than visiting a dedicated lab set up.

Furthermore, the disclosed VR game (the disclosed dual task paradigm) can be played with or without the VR head set. For the geriatric population, wearing the VR head for an immersive experience sometimes for some subjects might create difficulties, as the VR headset is bit heavy and can generate motion sickness. So, in such scenarios, the subject can opt for the non-immersive environment without VR headset. In the non-immersive environment, the subject can observe or look at his/her avatar on a display screen such as a large computer display or a TV display. The subject can continue with the game observing the display screen and to perform the dual task paradigm. In this scenario, two game applications for the dual task paradigm to be performed may run in parallel one on a server and another on a personal device of the subject. For example, one is server application, which takes input from the set of sensors (Kinect™), while another is client application, which is deployed on mobile phone or desktop (personal device). The client application can then obtain data corresponding to the set of sensors (for example, Kinect™ data) through server application running on the server.

In another use case scenario, the disclosed method can be applied for sports scenario such as 'running' capability of a sport person recovering from injury, wherein 'running' can be looked upon as a series of single limb squat jump, which occurs repetitively and quickly. Here, if there is a requirement of SLS testing for the person, then person may be asked to play the game or perform the dual task paradigm as disclosed in the VR environment. If the person can do it efficiently, he/she will be ready for on ground testing.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for interpreting neural interplay involving proprioceptive adaptation during a dual task paradigm, the method comprising:

monitoring, by one or more hardware processors, a subject performing the dual task paradigm, wherein the dual task paradigm is performed by the subject with a lower limb, from both limbs of the subject, at predefined intervals for a predefined time period for interpreting the neural interplay involving proprioceptive adaptation in the lower limb of the subject while performing the dual task paradigm, wherein the dual task paradigm comprises:

simulating integration of a Single Limb Stance (SLS) functionality test for postural stability and a single limb collision avoidance task, in an adaptive Virtual Reality (VR) environment provided to the subject, wherein the subject is positioned on an object in the VR environment equipped with one of a VR head set for immersive environment and a display screen for non-immersive environment, Electromyography (EMG) sensors placed on muscles associated with ankle joints of both limbs of the subject, and wherein motion of the subject while performing the dual task paradigm is sensed using a set of motion sensors placed at a predefined distance from the object;

receiving, by the one or more hardware processors, data associated with the subject performing the dual task paradigm, wherein the data comprises metadata of an avatar of the subject from one of the VR head set when in immersive environment and the display screen when in non-immersive environment, data from the EMG sensors and data from the set of motion sensors, to estimate a plurality of model parameters for the subject, wherein the plurality of model parameters comprise a Centre of Mass (CoM) sway, a collision rate, a trajectory smoothness variation and a muscle co-activation of the subject for the dual task paradigm; and analyzing, by the by one or more hardware processors, variation in the CoM sway, the collision rate, the trajectory smoothness variation and the muscle co-activation estimated for the subject in accordance with the dual task paradigm performed by the subject at the predefined intervals for the predefined time period to interpret the neural interplay involving proprioceptive adaptation in the lower limb during the dual task paradigm, wherein analysis provides a task that subject prioritizes among postural stability and collision avoidance in the dual task paradigm.

2. The method of claim 1, wherein the analyzed variation in the CoM sway, the collision rate, the trajectory smoothness variation and the muscle co-activation provides interpreting of the neural interplay involving proprioceptive adaptation in the lower limb of the subject is used to design personalized rehabilitation therapy for the subject.

3. The method of claim 1, wherein the dual task paradigm integrating the SLS functionality test for postural stability and the single limb collision avoidance task in the adaptive VR environment provided to the subject further comprises:
instructing the subject to stand on the object with both the limbs resting on the object;
displaying to the subject, using the VR head set, trail of control lines and obstacles of a predefined height approaching the avatar in the VR environment;
instructing the subject to lift the lower limb for a SLS posture when both limbs of the avatar touch a control line in the approaching trail and hold the SLS posture till an obstacle in the trail is crossed over by the avatar; and
notifying the subject of success or failure in maintaining the SLS posture and crossing of the obstacle along with a feedback to the subject for corrective action improve the collision avoidance in the SLS posture.

4. A system for interpreting neural interplay involving proprioceptive adaptation during a dual task paradigm, the system comprising:
a memory storing instructions;
one or more Input/Output (I/O) interfaces; and
one or more hardware processors coupled to the memory via the one or more I/O interfaces, wherein the one or more hardware processors are configured by the instructions to:
monitor a subject performing the dual task paradigm, wherein the dual task paradigm is performed by the subject with a lower limb, from both limbs of the subject, at predefined intervals for a predefined time period for interpreting the neural interplay involving proprioceptive adaptation in the lower limb of the subject while performing the dual task paradigm,
wherein the dual task paradigm comprises:
simulating integration of a Single Limb Stance (SLS) functionality test for postural stability and a single limb collision avoidance task, in an adaptive Virtual Reality (VR) environment provided to the subject, wherein the subject is positioned on an object in the VR environment equipped with one of a VR head set for immersive environment and a display screen for non-immersive environment, Electromyography (EMG) sensors placed on muscles associated with ankle joints of both limbs of the subject, and wherein motion of the subject while performing the dual task paradigm is sensed using a set of motion sensors placed at a predefined distance from the object;
receive data associated with the subject performing the dual task paradigm, wherein the data comprises metadata of an avatar of the subject from one of the VR head set when in immersive environment and the display screen when in non-immersive environment, data from the EMG sensors and data from the set of motion sensors, to estimate a plurality of model parameters for the subject, wherein the plurality of model parameters comprise a Centre of Mass (CoM) sway, a collision rate, a trajectory smoothness variation and a muscle co-activation of the subject for the dual task paradigm; and
analyze variation in the CoM sway, the collision rate, the trajectory smoothness variation and the muscle co-activation estimated for the subject in accordance with the dual task paradigm performed by the subject at the predefined intervals for the predefined time period to interpret the neural interplay involving proprioceptive adaptation in the lower limb during the dual task paradigm, wherein analysis provides a task that subject prioritizes among postural stability and collision avoidance in the dual task paradigm.

5. The system of claim 4, wherein the one or more hardware processors are configured to analyze variation in the CoM sway, the collision rate, the trajectory smoothness variation and the muscle co-activation provides interpreting of the neural interplay involving proprioceptive adaptation in the lower limb of the subject is used to design personalized rehabilitation therapy for the subject.

6. The system of claim 4, wherein the one or more hardware processors are configured to:
instruct the subject to stand on the object with both the limbs resting on the object;
display to the subject, using the VR head set, trail of control lines and obstacles of a predefined height approaching the avatar in the VR environment;
instruct the subject to lift the lower limb for a SLS posture when both limbs of the avatar touch a control line in the approaching trail and hold the SLS posture till an obstacle in the trail is crossed over by the avatar; and
notify the subject of success or failure in maintaining the SLS posture and crossing of the obstacle along with a feedback to the subject for corrective action improve the collision avoidance in the SLS posture.

7. One or more non-transitory machine readable information storage media comprising one or more instructions which when executed by one or more hardware processors causes a method for:
monitoring a subject performing the dual task paradigm, wherein the dual task paradigm is performed by the subject with a lower limb, from both limbs of the subject, at predefined intervals for a predefined time period for interpreting the neural interplay involving proprioceptive adaptation in the lower limb of the subject while performing the dual task paradigm,
wherein the dual task paradigm comprises:
simulating integration of a Single Limb Stance (SLS) functionality test for postural stability and a single limb collision avoidance task, in an adaptive Virtual Reality (VR) environment provided to the subject, wherein the subject is positioned on an object in the VR environment equipped with one of a VR head set for immersive environment and a display screen for non-immersive environment, Electromyography (EMG) sensors placed on muscles associated with ankle joints of both limbs of the subject, and wherein motion of the subject while performing the dual task paradigm is sensed using a set of motion sensors placed at a predefined distance from the object;

receiving data associated with the subject performing the dual task paradigm, wherein the data comprises metadata of an avatar of the subject from one of the VR head set when in immersive environment and the display screen when in non-immersive environment, data from the EMG sensors and data from the set of motion sensors, to estimate a plurality of model parameters for the subject, wherein the plurality of model parameters comprise a Centre of Mass (CoM) sway, a collision rate, a trajectory smoothness variation and a muscle co-activation of the subject for the dual task paradigm; and analyzing variation in the CoM sway, the collision rate, the trajectory smoothness variation and the muscle co-activation estimated for the subject in accordance with the dual task paradigm performed by the subject at the predefined intervals for the predefined time period to interpret the neural interplay involving proprioceptive adaptation in the lower limb during the dual task paradigm, wherein analysis provides a task that subject prioritizes among postural stability and collision avoidance in the dual task paradigm.

8. The one or more non-transitory machine readable information storage media of claim 7, wherein the analyzed variation in the CoM sway, the collision rate, the trajectory smoothness variation and the muscle co-activation provides interpreting of the neural interplay involving proprioceptive adaptation in the lower limb of the subject is used to design personalized rehabilitation therapy for the subject.

9. The one or more non-transitory machine readable information storage media of claim 7, wherein the dual task paradigm integrating the SLS functionality test for postural stability and the single limb collision avoidance task in the adaptive VR environment provided to the subject further comprises:

instructing the subject to stand on the object with both the limbs resting on the object;

displaying to the subject, using the VR head set, trail of control lines and obstacles of a predefined height approaching the avatar in the VR environment;

instructing the subject to lift the lower limb for a SLS posture when both limbs of the avatar touch a control line in the approaching trail and hold the SLS posture till an obstacle in the trail is crossed over by the avatar; and notifying the subject of success or failure in maintaining the SLS posture and crossing of the obstacle along with a feedback to the subject for corrective action improve the collision avoidance in the SLS posture.

\* \* \* \* \*